(12) United States Patent
MacQuarrie

(10) Patent No.: US 7,678,397 B2
(45) Date of Patent: Mar. 16, 2010

(54) EDIBLE DISSOLVING GELATIN STRIPS

(76) Inventor: Reg MacQuarrie, 345 Prince Edward Drive N., Toronto, Ontario (CA) M8X 2L4

( * ) Notice: Subject to any disclaimer, the term of this patent is extended or adjusted under 35 U.S.C. 154(b) by 0 days.

(21) Appl. No.: 11/976,926

(22) Filed: Oct. 30, 2007

(65) Prior Publication Data

US 2008/0063779 A1     Mar. 13, 2008

Related U.S. Application Data

(63) Continuation of application No. 11/418,027, filed on May 5, 2006, now abandoned, which is a continuation-in-part of application No. 10/695,905, filed on Oct. 30, 2003, now abandoned.

(60) Provisional application No. 60/422,123, filed on Oct. 30, 2002.

(51) Int. Cl.
*C08L 5/00* (2006.01)
*A22C 13/00* (2006.01)

(52) U.S. Cl. .................. 426/103; 426/105; 426/138; 426/534; 426/576; 426/578; 426/661

(58) Field of Classification Search ................. 426/103, 426/105, 138, 534, 576, 578, 661
See application file for complete search history.

(56) References Cited

U.S. PATENT DOCUMENTS

| 5,419,916 | A | 5/1995 | Yamamoto et al. |
| 6,274,162 | B1 * | 8/2001 | Steffenino et al. .......... 424/439 |
| 6,730,340 | B1 * | 5/2004 | Macquarrie et al. ......... 426/105 |

FOREIGN PATENT DOCUMENTS

| EP | 0 460 588 A1 | | 12/1991 |
| EP | 0 547 551 A1 | | 6/1993 |
| EP | 547551 | * | 6/1993 |
| WO | WO 96/14753 | | 5/1996 |
| WO | WO 00/67582 | * | 11/2000 |

OTHER PUBLICATIONS

PCT International Search Report dated May 3, 2004, issued in International Application No. PCT/CA03/01663—Filed: Oct. 30, 2003 (4 pages).

* cited by examiner

*Primary Examiner*—Brian P Mruk
(74) *Attorney, Agent, or Firm*—Dinesh Agarwal, P.C.

(57) ABSTRACT

Orally disintegrating or dissolving edible strips for use as a matrix for retaining and delivering nutrients, flavors and medicinal compounds are made from new liquid film casting compositions comprising a major proportion of gelatin. The particularly low melting range for hydrated gelatin produces films that leave virtually no residue upon dissolving in the mouth and can be used in the form of thicker films and strips than known edible films.

11 Claims, No Drawings

EDIBLE DISSOLVING GELATIN STRIPS

RELATED APPLICATION

This is a continuation of application Ser. No. 11/418,027, filed May 5, 2006, now abandoned which is a continuation-in-part of application Ser. No. 10/695,905, filed Oct. 30, 2003 now abandoned, which claims priority based on U.S. provisional patent application No. 60/422,123, filed Oct. 30, 2002, all incorporated herein in their entirety by reference.

BACKGROUND OF THE INVENTION

Orally disintegrating or dissolving edible materials are currently used in a large variety of applications as a matrix for conveniently holding and using nutrients, flavors and medicinal compounds such as breath fresheners. The slow-dissolving edible strips currently in use are typically produced from pullulan, sodium alginate, starches, carrageenans or combinations of these ingredients. All of these are suitable film forming materials which dissolve adequately, but they tend to leave an undesirable gummy residue in the mouth that remains for a greater or lesser period of time after the film structure has broken down and the matrix has released its contents.

I have found that gelatin, widely used in a number of candy applications, is unusually suitable as the major film component of edible film materials, for use as edible dissolving strips.

Gelatin, in particular high bloom gelatin, is an excellent film former and can readily be cast into film form. Unique among the hydrocolloids, gelatin melts at approximately 37° C., with the result that an edible strip composed primarily of gelatin dissolves and melts in the mouth without leaving any of the unpleasant residue associated with polysaccharide films. A consequence of the unique melting property of gelatin is that films can be made thicker than films composed of other materials used for this purpose. Typical polysaccharide films in edible dissolving strips are less than 35 microns in thickness, whereas gelatin-based films can be used for this purpose with thicknesses as great as 85 microns. The thicker films do tend to dissolve more slowly, but still melt into their gelatin content, resulting in a pleasant sensation in the mouth.

DESCRIPTION OF THE INVENTION

The present invention is directed to edible dissolving film of a material comprising gelatin in combination with lesser proportions of plasticizers and selected flavors, medicinal compounds or nutrients, as desired.

To prepare films according to the present invention, gelatin and the other ingredients are dissolved in water under high shear. If hot-water gelatin is employed, then the polymers must be dissolved at elevated temperatures to ensure that the gelatin will hydrate property. As the polymers become fully hydrated, additional additives can be introduced including plasticizers, flavors, various salts, medicinal compounds and colors. Where necessary, the gelatin in solution can be cooled down to ambient temperatures prior to the addition of volatile flavors or organic materials, to reduce the amount of potential "flash off" and consequent diminishment of flavor in the solution.

As the solution is cooled, its viscosity increases and it becomes easier to cast onto a steel belt or plastic web as required. Typically, the hot solution is cast onto the web by the use either of a box or conventional closed die. On the web this solution is dried to the desired moisture level for stability and the dried film is then removed from the web on the plastic vacuum, to be cut into strips for consumption.

The film can also be produced using standard film extrusion techniques employing either a single-screw or twin screw extruder.

It is expected that most products made up of films according to the present invention will be strips, but using known film extrusion techniques films according to the present invention can be extruded into tubular or other shapes. The film can also be formed into bags by sealing edges together. Such bags or pouches might be used to contain other sweeteners, flavored powders or solutions. For example, a small bag produced from edible film according to the invention encapsulating liquid flavoring dissolved in an edible oil or propylene glycol will dissolve in the mouth, releasing the liquid flavoring as a "secondary" flavor sensation for the consumer.

The gelatin film forming base can be augmented with smaller amounts of other polymers to modify the characteristics of the final film to meet the demands of particular applications. However, the proportion of other polymers that can be added should be kept low to minimize any left over residue following dissolution of the film structure.

Suitable polymers for addition to the gelatin in producing edible dissolving strips according to the present invention include starch (tapioca), low molecular weight corn and potato starches, alginates, lambda carrageenans, and various other polysaccharides. For optimum solubility of the film, the composition should be such that the gelatin component makes up at least 50% by weight of the total composition of the film formers.

Some variation in properties for different applications can be achieved by using gelatins having a variety of bloom strengths (gel strengths) and different provenance, including bovine, porcine and fish gelatins. The use of cold-water soluble gelatin aids in production of the film by obviating the necessity of heating the solution.

The film can be also sweetened with traditional sweeteners including sucralose, aspartame, ascuefame K and other artificial sweeteners.

The film may advantageously be plasticized by the addition of a polyol such as sorbital or other sugar alcohols. Glycerine or propylene glycol may also be used.

Gelatin-based films according to the present invention can be easily flavored with all manner of natural and artificial flavors including menthols and other cooling agents. The loads on such flavorings can be adjusted as required. The total load of oil-based flavors can range as high as 25% of the total composition but are normally optimized below 15% of the total composition based on weight.

EXAMPLES

Examples 1 to 3 below illustrate specific compositions within the present invention.

|   | % |
| --- | --- |
| Example 1 | |
| Gelatin (100 bloom) | 76 |
| Sorbitol | 3 |
| Water | 6 |
| Flavor-L-menthol | 10 |
| Peppermint | 3 |
| Mono and diglycerides | 2 |

-continued

|  | % |
| --- | --- |
| Example 2 | |
| Gelatin (250 bloom) | 81 |
| Sorbitol | 3 |
| Water | 8 |
| Polysorbate 80 | 3 |
| Flavor - Mango | 5 |
| Example 3 | |
| Gelatin (250 bloom) | 82 |
| Sweetener (Sucralose) | 0.80 |
| Sorbitol | 4 |
| Glycerin | 7.0 |
| Sorbitan ester | 1.5 |
| Color | .02 |
| Water | 4.6 |

Examples 4 to 6 below illustrate specific compositions within the present invention, where the gelatin content is less than or below 45% of the total composition.

The main advantage of having the gelatin content below 45% is that it increases the melt point of the strip or film and improves the film's resistance to humidity, while maintaining the desired mouth feel.

There are several critical aspects of thin films used for confections: 1) The film must dissolve quickly in the mouth without pasting; 2) The film needs to be as resistant as possible to curling caused by exposure to high humidity; and, 3) The films should not block or stick to each other in a packaged environment.

If a film is made entirely of gelatin it will dissolve very well, gelatin melts at 37° C., and consequently it will provide excellent mouth feel.

The problem with films composed of high gelatin contact is that they tend to be very susceptible to moisture absorption and curl readily. In addition, the films become very tacky as they absorb moisture and this results in the blocking of films.

The optimized formulations, illustrated below in Examples 4-6, reduce the gelatin content to the level where it is still a large enough proportion to give the desired mouth feel, but it is below the levels where blocking and product distortion occur.

|  | % |
| --- | --- |
| Example 4 - Sour Grape Strip | |
| Gelatin (260 bloom) | 37 |
| Tartaric acid | 30 |
| Alginate | 11 |
| Water | 8 |
| Grape Flavor | 4.5 |
| Sorbitol | 2.7 |
| Glycerine | 1.3 |
| Modified Starch | 1.33 |
| Carrageenan | 1.32 |
| Sorbitan Mono Stearate | 1.3 |
| Sucralose | 0.5 |
| Aspartame | 0.4 |
| Acesulfame Potassium | 0.4 |
| Color Red#40 | 0.15 |
| Blue #1 | 0.1 |
| Example 5 - Peppermint | |
| Alginate | 22.0 |
| Gelatin | 24.5 |
| Sorbitol | 15 |

-continued

|  | % |
| --- | --- |
| Modified Cellulose | 8 |
| Water | 8 |
| Peppermint Flavor | 7 |
| Menthol | 4 |
| Xylitol | 3.8 |
| Sorbiton Mono Stearate | 3.7 |
| Aspartame | 1.5 |
| Acesulfame Potassium | 1.45 |
| Glycerin | 1 |
| Color | 0.05 |
| Example 6 - Peppermint Zinc Gluconate | |
| Zinc Gluconate | 21.5 |
| Alginate | 14 |
| Gelatin | 18 |
| Sorbitol | 14 |
| Modified Cellulose | 12 |
| Water | 7.5 |
| Peppermint Flavor | 4 |
| Menthol | 3 |
| Xylitol | 2.7 |
| Sorbiton Mono Stearate | 2.7 |
| Aspartame | 0.2 |
| Acesulfame Potassium | 0.2 |
| Glycerin | 0.19 |
| Color | 0.01 |

Although specific film compositions have been given as examples of materials within the present invention, it will be understood that it is the novel inclusion of a major portion of gelatin in edible film forming materials that affords unique advantages over the film-forming materials conventionally used to make edible matrices in strips and other forms. No unnecessary limitations should be understood from the examples given, as modifications will be obvious to those of skill in the art without departure from the scope and spirit of the appended claims.

I claim:

1. An edible, orally dissolvable film, comprising at least 76% by weight of a medium or high bloom gelatin, one or more flavoring materials, an edible polyol plasticizer and water.

2. The film according to claim 1, further comprising an artificial sweetener.

3. The film according to claim 2, wherein said gelatin comprises a 100 or more bloom gelatin.

4. The film according to claim 2, further comprising an edible polymer selected from the group consisting of tapioca starch, low molecular weight corn starch, low molecular weight potato starch, alginates, and lambda carrageenans.

5. The film according to claim 2, wherein said plasticizing polyol comprises glycerine.

6. The film according to claim 2, wherein said plasticizing polyol comprises propylene glycol.

7. The film according to claim 1, wherein said flavoring materials comprise artificial oils making up less than 15% by weight of the film.

8. The film according to claim 2, prepared by solution casting or extrusion.

9. A film according to claim 7, having a thickness between 35 microns and 85 microns.

10. The film according to claim 4, further comprising modified cellulose.

11. The film according to claim 1, wherein said polyol plasticizer comprises less than 5% by weight of the film.

* * * * *